United States Patent
Millien-White

(10) Patent No.: US 9,161,725 B1
(45) Date of Patent: Oct. 20, 2015

(54) ADJUSTABLE BREAST EXAMINATION DEVICE

(71) Applicant: Regine Millien-White, Cambria Heights, NY (US)

(72) Inventor: Regine Millien-White, Cambria Heights, NY (US)

( * ) Notice: Subject to any disclaimer, the term of this patent is extended or adjusted under 35 U.S.C. 154(b) by 0 days.

(21) Appl. No.: 14/173,093

(22) Filed: Feb. 5, 2014

(51) Int. Cl.
*A61B 6/04* (2006.01)
*A61B 6/00* (2006.01)

(52) U.S. Cl.
CPC .. *A61B 6/04* (2013.01); *A61B 6/502* (2013.01)

(58) Field of Classification Search
CPC ........ A61B 6/502; A61B 6/0414; A61B 6/06; A61B 6/4233; A61B 6/0435; A61B 5/708; A61B 8/0825; A61B 8/406; A61B 10/0041; A61B 5/0091; A61B 2019/205
USPC .......................................................... 378/37
See application file for complete search history.

(56) References Cited

U.S. PATENT DOCUMENTS

| | | | |
|---|---|---|---|
| 5,569,266 A | 10/1996 | Siczek | |
| 7,597,104 B2 | 10/2009 | Zheng et al. | |
| D615,278 S | 5/2010 | Reed | |
| 7,831,015 B2 | 11/2010 | Li et al. | |
| 8,014,490 B2 | 9/2011 | Mitchell et al. | |
| 2004/0073106 A1 | 4/2004 | Lee et al. | |
| 2006/0256928 A1* | 11/2006 | Grosse | 378/189 |
| 2009/0238332 A1* | 9/2009 | Farrell-Trent | 378/37 |
| 2010/0041979 A1 | 2/2010 | Harter | |
| 2010/0080343 A1* | 4/2010 | Kalender et al. | 378/37 |
| 2010/0177866 A1* | 7/2010 | Shibuya | 378/20 |
| 2010/0246760 A1* | 9/2010 | Li et al. | 378/37 |

FOREIGN PATENT DOCUMENTS

| | | |
|---|---|---|
| KR | 1020110026288 | 3/2011 |
| WO | WO2006119426 | 11/2006 |

* cited by examiner

*Primary Examiner* — Glen Kao
*Assistant Examiner* — Chih-Cheng Kao

(57) ABSTRACT

An adjustable breast examination device enhances comfort for an individual by adjusting to accommodate variously sized breasts. The device includes a slot extending into a housing. Each of a plurality of plates is interchangeably positionable in the slot. Each plate has a respective cavity extending into a surface of the plate such that each plate may receive a human breast in the cavity. Each cavity is uniquely sized relative to each other the cavity wherein the plates correspond to a plurality of unique breast sizes. An examination mechanism is coupled to the housing and positioned such that the examination mechanism examines the human breast positioned in the cavity of a selected one of the plates positioned in the slot.

12 Claims, 4 Drawing Sheets

ADJUSTABLE BREAST EXAMINATION DEVICE

BACKGROUND OF THE DISCLOSURE

Field of the Disclosure

The disclosure relates to breast examination devices and more particularly pertains to a new breast examination device for enhancing comfort for an individual by adjusting to accommodate variously sized breasts.

SUMMARY OF THE DISCLOSURE

An embodiment of the disclosure meets the needs presented above by generally comprising a slot extending into a housing. Each of a plurality of plates is interchangeably positionable in the slot. Each plate has a respective cavity extending into a surface of the plate such that each plate may receive a human breast in the cavity. Each cavity is uniquely sized relative to each other the cavity wherein the plates correspond to a plurality of unique breast sizes. An examination mechanism is coupled to the housing and positioned such that the examination mechanism examines the human breast positioned in the cavity of a selected one of the plates positioned in the slot.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
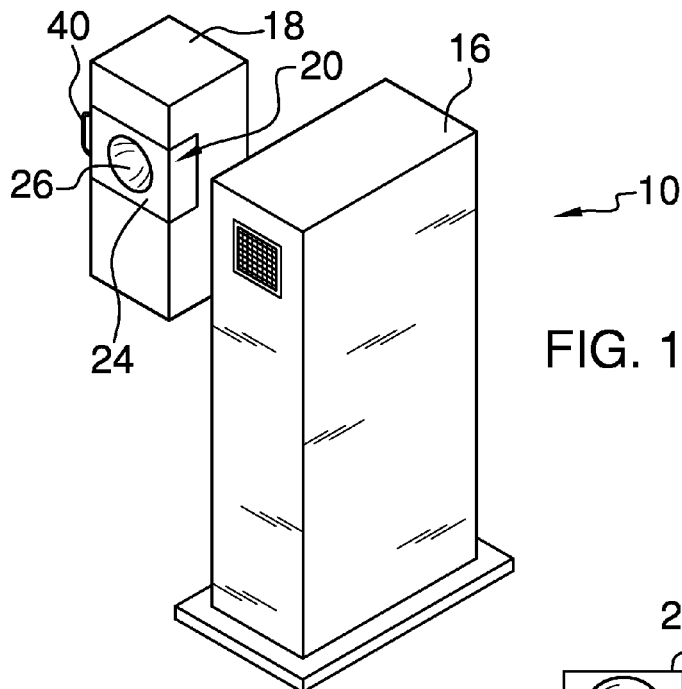
FIG. 1 is a top front side perspective view of a adjustable breast examination device according to an embodiment of the disclosure.
Figure 2:
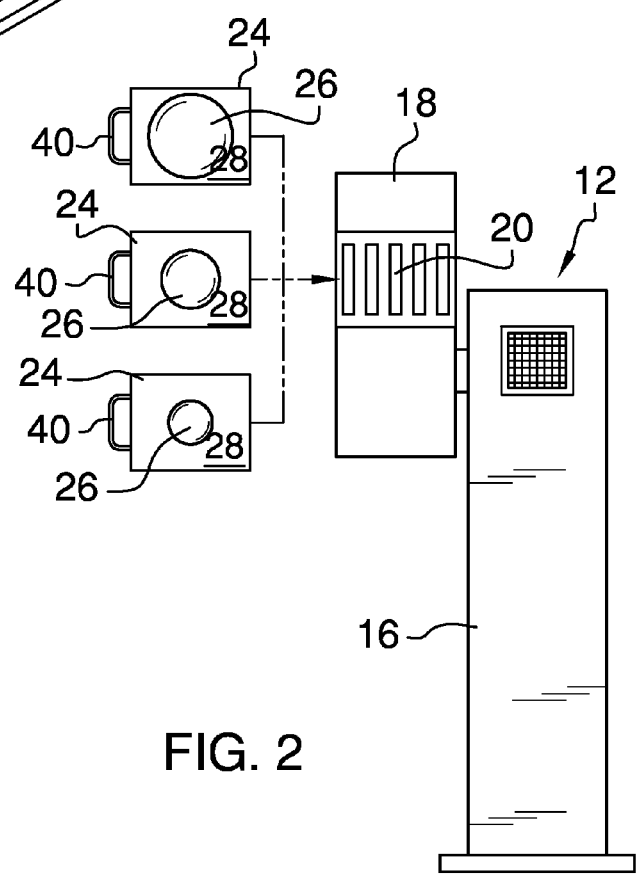
FIG. 2 is a partially exploded front view of an embodiment of the disclosure.
Figure 3:
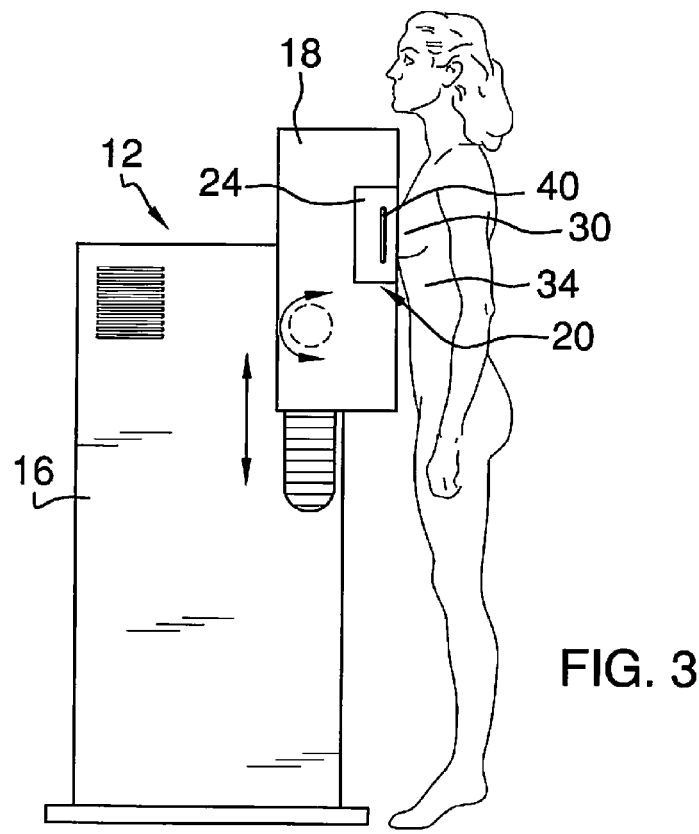
FIG. 3 is a side view of an embodiment of the disclosure in use.
Figure 4:
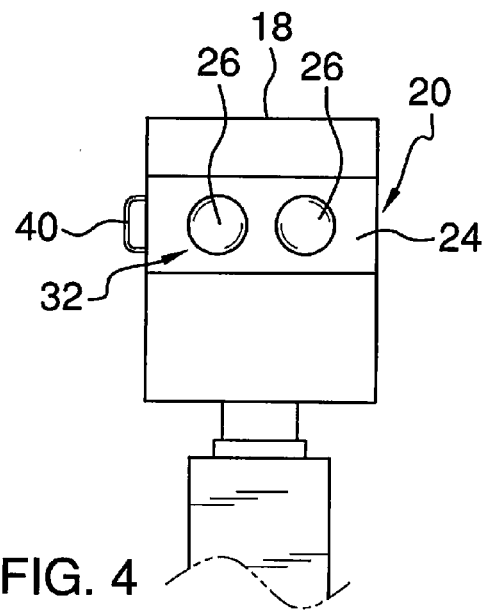
FIG. 4 is a detailed front view of an embodiment of the disclosure.
Figure 5:
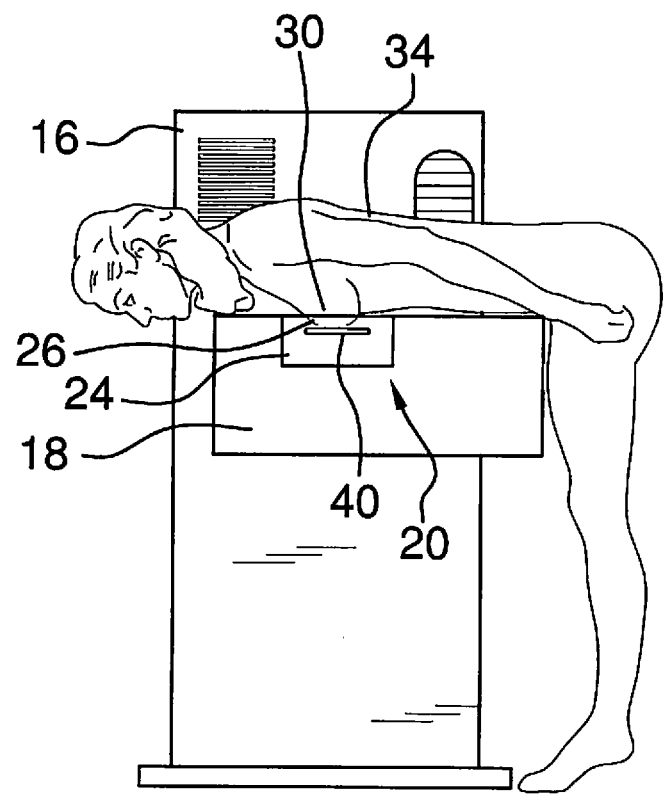
FIG. 5 is a side view of an embodiment of the disclosure.

With reference now to the drawings, and in particular to FIGS. 1 through 7 thereof, a new breast examination device embodying the principles and concepts of an embodiment of the disclosure and generally designated by the reference numeral 10 will be described.

Figure 6:
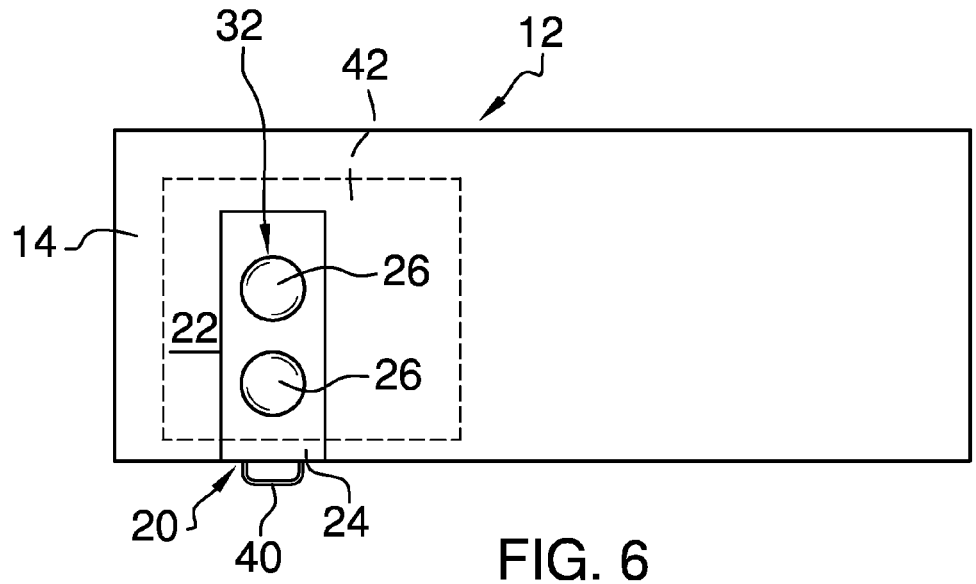
FIG. 6 is a top view of an embodiment of the disclosure.
Figure 7:
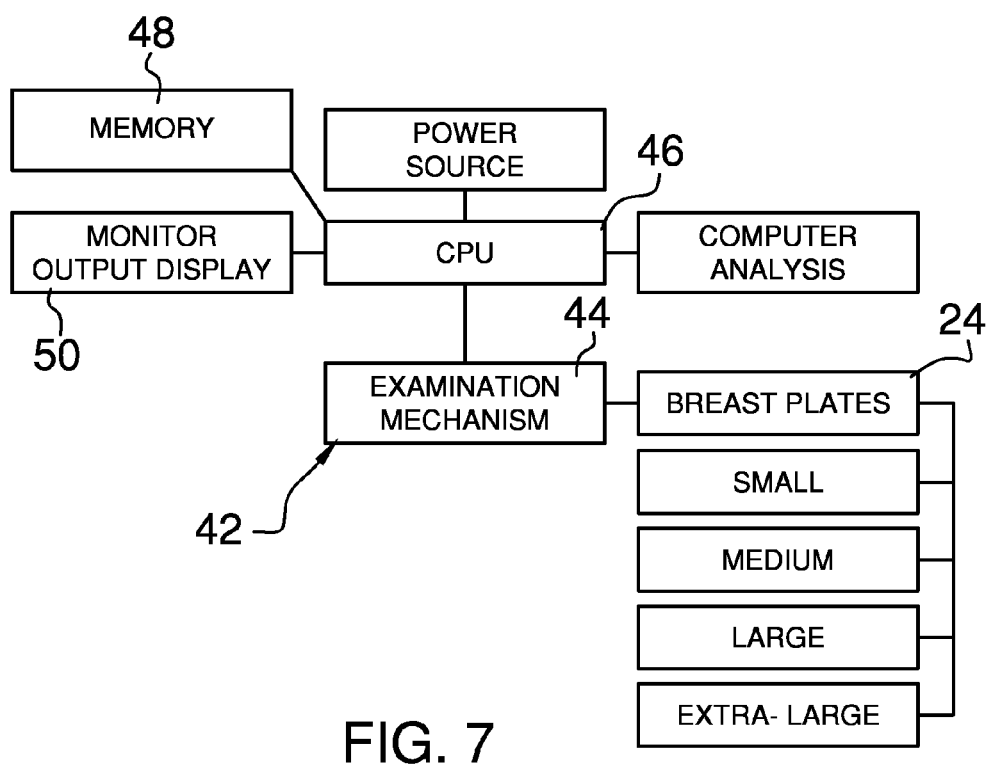
FIG. 7 is a schematic view of an embodiment of the disclosure.

As best illustrated in FIGS. 1 through 7, the adjustable breast examination device 10 generally comprises a housing 12. The housing 12 may comprise a unitary table 14, as shown in FIG. 6, or may comprise a main section 16 and an auxiliary section 18. The auxiliary section 18 is movably coupled to the main section 16 wherein a position of the auxiliary section 18 relative to the main section 16 is adjustable. The auxiliary section 18 is vertically adjustable wherein a height of the auxiliary section 18 is adjustable. The main section 16 may be weighted or fixed to a supporting surface such that the auxiliary section 18 forms a surface capable of supporting the weight of a person leaning completely on the auxiliary section 18.

A slot 20 extends into the housing 12. In the embodiment shown in FIG. 6, the slot 20 is positioned on a top surface 22 of the table 14. In the embodiment shown in FIGS. 1 through 5, the slot 20 is positioned in the auxiliary section 18. Each of a plurality of plates 24 is interchangeably positionable in the slot 20. Each plate 24 has at least one respective cavity 26 extending into a surface 28 of the plate 24 such that each plate 24 is configured for receiving one human breast 30 in the respective cavity 26. Each cavity 26 on each separate plate 24 is uniquely sized relative to each cavity 26 on each other plate 24 wherein the plates 24 are configured to correspond to a plurality of unique breast sizes. Each plate 24 may have a single cavity 26 or a pair 32 of the cavities 26. When two cavities 26 are provided, each pair 32 of the cavities 26 in each plate 24 may be substantially equivalent in size. Each plate 24 is horizontally oriented when the plate 24 is positioned in the slot 20. Thus, the cavity 26 in the plate 24 is configured to receive the human breast 30 extending from a torso 34 in a horizontal position allowing the breast 30 to hang from the torso 34 and be positioned in the cavity 26. The auxiliary section 18 may also be rotationally coupled to the main section 16 allowing for angling of the plate 24 relative to the main section 16 to more comfortably accommodate positioning of the breast 30 in the cavity 26 while a person is standing and leaning into or over the plate 24. Thus, a person may remain in a substantially standing position in the event being positioned horizontally is not comfortable or possible for any reason. Each of a plurality of handles 40 is coupled to an associated one of the plates 24 to facilitate manipulation of the plates 24 and insertion of each plate 24 into the slot 20. Each plate 24 may be retained in the slot 20 by a conventional mechanism such as a tongue and groove, retainer clip, or the like.

An examination mechanism 42 is coupled to the housing 12. The examination mechanism 42 is positioned such that the examination mechanism 42 is configured for examining the human breast 30 positioned in the cavity 26 of a selected one of the plates 24 positioned in the slot 20. The examination mechanism 42 may comprise an x-ray generator 44 for mammography or another conventional mechanism which may utilize the isolation and positioning of the breast 30 while pressed into the cavity 26. The examination mechanism 42 is configured for examining a pair of breasts 30 simultaneously while the pair of breasts 30 are positioned in the pair of cavities 26. A processor 46 may be communicatively coupled to the examination mechanism 42 to selectively operate the functions of and actuate the examination mechanism 42. A digital memory 48 is communicatively coupled to the processor 46 such that the processor 46 stores examination data on the digital memory 48 as desired. The examination data may be an image or other data generated by the examination mechanism 42. A monitor 50 may be communicatively coupled to the processor 46 such that the monitor 50 displays images generated by the examination mechanism 42 for immediate review.

In use, the device 10 is adjustable to accommodate variously sized breasts 30 while the person being examined is in a horizontal position. In an embodiment, the device 10 may be further adjusted to permit the person to remain in a substantially standing position while leaning into or over the auxiliary section 18 positioning at least one breast 30 into the cavity 26 of a selected one of the plates 24 corresponding to the size of the breast 30 being examined. Each cavity 26 may be formed to receive and distribute breast tissue into a shape necessary for or enhancing the data produced by the examination mechanism 42.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An adjustable breast examination device comprising:
    a housing;
    a slot extending into said housing;
    a plurality of plates, each plate being planar, said plates being interchangeably positionable in said slot, each said plate having a respective cavity extending into a surface of said plate inset from a peripheral edge of said plate such that each said plate is configured for receiving a human breast in said respective cavity, each said cavity being uniquely sized relative to each other said cavity wherein said plates are configured to correspond to a plurality of unique breast sizes; and
    an examination mechanism coupled to said housing, said examination mechanism being positioned such that said examination mechanism is configured for examining the human breast positioned in said cavity of a selected one of said plates positioned in said slot.

2. The device of claim 1, further comprising each said plate being horizontally oriented when said plate is positioned in said slot wherein said cavity in said plate is configured to receive the human breast extending from a torso in a horizontal position.

3. The device of claim 1, further comprising said housing comprising a main section and an auxiliary section, said slot being positioned in said auxiliary section.

4. The device of claim 3, further comprising said auxiliary section being movably coupled to said main section wherein a position of said auxiliary section relative to said main section is adjustable such that said plate is adjustable to a horizontal position.

5. The device of claim 4, further comprising said auxiliary section being vertically adjustable wherein a height of said auxiliary section is adjustable.

6. The device of claim 1, further comprising each said plate having a pair of said cavities, each pair of said cavities in each said plate being substantially equivalent in size, said examination mechanism being configured for examining a pair of breasts simultaneously while the pair of breasts are positioned in said pair of cavities.

7. The device of claim 1, further comprising a plurality of handles, each said handle being coupled to an associated one of said plates.

8. The device of claim 1, further comprising said examination mechanism comprising an x-ray generator.

9. The device of claim 1, further comprising:
    a processor communicatively coupled to said examination mechanism; and
    a digital memory communicatively coupled to said processor such that said processor stores examination data on said digital memory.

10. The device of claim 9, further comprising a monitor communicatively coupled to said processor such that said monitor displays images generated by said examination mechanism.

11. An adjustable breast examination device comprising:
    a housing, said housing comprising a main section and an auxiliary section, said auxiliary section being movably coupled to said main section wherein a position of said auxiliary section relative to said main section is adjustable, said auxiliary section being vertically adjustable wherein a height of said auxiliary section is adjustable;
    a slot extending into said housing, said slot being positioned in said auxiliary section such that said slot is adjustable to be in a horizontal position;
    a plurality of plates, each said plate being planar, said plates being interchangeably positionable in said slot such that said plate is horizontally oriented, each said plate having a respective cavity extending into a surface of said plate inset from a peripheral edge of said plate such that each said plate is configured for receiving a human breast in said respective cavity, each said cavity being uniquely sized relative to each other said cavity wherein said plates are configured to correspond to a plurality of unique breast sizes, each said plate being horizontally oriented when said plate is positioned in said slot wherein said cavity in said plate is configured to receive the human breast extending from a torso in a horizontal position;
    a plurality of handles, each said handle being coupled to an associated one of said plates;
    an examination mechanism coupled to said housing, said examination mechanism being positioned such that said examination mechanism is configured for examining the human breast positioned in said cavity of a selected one of said plates positioned in said slot, said examination mechanism comprising an x-ray generator;
    a processor communicatively coupled to said examination mechanism;
    a digital memory communicatively coupled to said processor such that said processor stores examination data on said digital memory; and
    a monitor communicatively coupled to said processor such that said monitor displays images generated by said examination mechanism.

12. The device of claim 11, further comprising each said plate having a pair of said cavities, each pair of said cavities in each said plate being substantially equivalent in size, said examination mechanism being configured for examining a pair of breasts simultaneously while the pair of breasts are positioned in said pair of cavities.

\* \* \* \* \*